(12) United States Patent
Koplin et al.

(10) Patent No.: US 11,780,996 B2
(45) Date of Patent: Oct. 10, 2023

(54) BREATHABLE FILM

(71) Applicant: RKW SE, Mannheim (DE)

(72) Inventors: Robert Koplin, Dittenheim (DE); Dennis Becker, Ansbach (DE); Christoph Meier, Dittenheim (DE); Thomas Arlt, Heilsbronn (DE)

(73) Assignee: RKW SE, Mannheim (DE)

( * ) Notice: Subject to any disclaimer, the term of this patent is extended or adjusted under 35 U.S.C. 154(b) by 197 days.

(21) Appl. No.: 17/422,620

(22) PCT Filed: May 2, 2020

(86) PCT No.: PCT/EP2020/062225
§ 371 (c)(1),
(2) Date: Jul. 13, 2021

(87) PCT Pub. No.: WO2020/225165
PCT Pub. Date: Nov. 12, 2020

(65) Prior Publication Data
US 2022/0089846 A1 Mar. 24, 2022

(30) Foreign Application Priority Data
May 3, 2019 (DE) .......... 102019111445.4

(51) Int. Cl.
*C08L 23/06* (2006.01)
*B29C 49/00* (2006.01)
*B29C 49/04* (2006.01)
*B29C 49/42* (2006.01)
*B29C 55/04* (2006.01)
*B29K 23/00* (2006.01)
*C08L 23/12* (2006.01)

(52) U.S. Cl.
CPC .......... *C08L 23/06* (2013.01); *B29C 49/0005* (2013.01); *B29C 49/04* (2013.01); *B29C 49/4273* (2013.01); *B29C 55/04* (2013.01); *B29K 2023/0633* (2013.01); *C08L 23/12* (2013.01); *C08L 2203/16* (2013.01); *C08L 2205/025* (2013.01); *C08L 2205/03* (2013.01)

(58) Field of Classification Search
CPC ...... C08L 23/06; C08L 23/08; C08L 23/0807; C08L 23/0815; A61F 13/51548; C08J 5/18
See application file for complete search history.

(56) References Cited

U.S. PATENT DOCUMENTS

| | | | |
|---|---|---|---|
| 3,156,242 A | 11/1964 | Crowe, Jr. | |
| 3,881,489 A | 5/1975 | Hartwell | |
| 5,015,521 A * | 5/1991 | Fujii | ........................ C08J 5/18 521/134 |
| 5,695,868 A | 12/1997 | McCormack | |
| 8,834,437 B2 | 9/2014 | Borrero et al. | |
| 9,216,116 B2 | 12/2015 | Roe et al. | |
| 10,022,280 B2 | 7/2018 | Ehrnsperger et al. | |
| 2002/0143306 A1 | 10/2002 | Tucker et al. | |
| 2005/0267429 A1 | 1/2005 | Cohen | |
| 2019/0076266 A1 * | 3/2019 | Trudeau | .................. A61F 2/28 |

FOREIGN PATENT DOCUMENTS

| | | |
|---|---|---|
| CN | 106397918 | 2/2017 |
| DE | 69719574 | 9/2003 |
| EP | 0232060 | 8/1987 |
| EP | 3176204 | 6/2017 |
| EP | 3222406 | 9/2017 |
| WO | 2015175593 | 11/2015 |

OTHER PUBLICATIONS

Thomson Scientific, London, GB; , vol. 2017, No. 27, AN 2017-13236P, Retrieved from: Database WPI [online] XP002799962.

* cited by examiner

*Primary Examiner* — Jeffrey C Mullis
(74) *Attorney, Agent, or Firm* — Volpe Koenig

(57) ABSTRACT

A breathable film having a specific ball-drop impact resistance of more than 100 mm per gram polymer per square meter. The film has a water vapor permeability of at least 1000 g/m2 in 24 hours. The elongation at break of the film in the machine direction is less than 200%.

15 Claims, No Drawings

BREATHABLE FILM

TECHNICAL FIELD

The invention relates to a breathable film, to a process for production thereof, and to the use thereof as a backsheet in diapers.

BACKGROUND

In single-use diapers the outside is formed from a liquid impermeable film which prevents escape of excretions. The film forms a layer which is arranged facing away from the carrier and is referred to as a "backsheet". Gas-impermeable plastic films were initially used, but breathable films have now been employed for a long time. These liquid-impermeable but simultaneously water vapor-permeable films markedly improve the wear comfort of the diapers since the breathability allows self-drying of the diapers which prevents the diapers feeling hot to wear.

In addition, the breathability also counters diaper dermatitis. The removal of moisture brings about a more skin-friendly climate in the diaper and skin irritation is therefore markedly reduced.

The use of vapor-permeable substrates was described as early as 1964 in U.S. Pat. No. 3,156,242, where a microporous film is used.

U.S. Pat. No. 3,881,489 from 1975 describes a breathable substrate comprising a combination of two layers of which the first is a perforated thermoplastic film having a low empty volume and the second is a porous hydrophobic thin material having a high empty volume.

Although these developments of breathable substrates provided a certain extent of improvement compared to impermeable substrates, films with more effective vapor permeability which at the same time effectively prevent escape of liquid have subsequently been sought.

EP 0 232 060 B1 from 1987 describes a process for producing a gas-permeable porous film by introduction of inorganic filling material and subsequent stretching of the film.

There have since been numerous developments of such filled breathable films since the demands on the use of breathable, liquid-tight films in hygiene sectors in a global market are ever increasing. Thus what is required is liquid tightness coupled with high water vapor permeability. Insufficient water vapor permeability would result in a hot, sticky, skin-unfriendly product which would not be accepted by the consumer.

Furthermore, modern backsheet films must exhibit properties such as softness, suppleness, low crackle, and an ideally textile grip.

In single-use diapers it is desirable to provide graphic designs on the articles. It has been found that a high whiteness is very important to the consumer. Consumers are not accepting of a yellowish or off-white shade. A high whiteness appears high-quality and is essential to the sales success of the diaper. Backsheet films are therefore required to exhibit a high opacity.

In addition to the high opacity of the film, the design of baby diapers is defined essentially by brand- and size-specific printed designs. While motifs in the past were often simple repeat prints, nowadays registered prints, where all printed elements are positioned at a precisely defined site on the diaper, are customary. The very fast-running diaper converters place high demands on registration accuracy since variations in the register length can result in loss of synchronization between the backsheet and the converter which may result in the diapers needing to be discarded.

Diaper design has also undergone development at great speed in recent years. Thus, the absorbent bodies present in the diapers have become ever thinner, which has been made possible especially through the use of superabsorbers. These superabsorbers are employed in the form of large particle size powders. Despite the use of these large particle size materials, penetration of the film by individual particles must be effectively prevented. High demands are therefore placed on the penetration resistance of the backsheets so that escape of excretions is effectively prevented.

Simultaneously, for resource conservation and sustainability, the films shall be as thin as possible and in filled films the polymer proportion shall be as low as possible.

On the diaper exterior a nonwoven material is generally applied to the film to impart fabric-like haptics. The basis weight of the employed nonwoven is likewise ever further reduced for reasons of resource conservation. Especially when the diaper is donned and the elastic ears on the diaper back side are drawn around the body to close the diaper, a significant tensile force in the cross direction is exerted and must be absorbed by the laminate consisting of the breathable film and the nonwoven. If the basis weight of the nonwoven is reduced, the film must absorb more force. Conventional films are unsuitable therefor.

A further requirement of backsheet films is the minimum tensile strength required for processing of the film web on the extremely fast-moving diaper production machines (converters). The throughput of diapers manufactured is ever increasing. While speeds of 600 diapers per minute were customary some years ago, plants for 1000 diapers per minute or more are employed today. Increasing line speed results in higher force peaks being exerted on the film. Thus very high demands are placed on the films, especially during folding of the finished diapers and subsequent compression when the air is squeezed out of the diaper.

In addition, recent changes in diaper design result in high point stresses on the backsheet film. Both the design of the absorbent cores with channels, as described for example in U.S. Pat. No. 9216116 B2, and the design of thinner absorbent cores, as described for example in U.S. Pat. No. 10022280 B2, result in increasing stresses on the backsheet film. The backsheet film must also withstand higher proportions of superabsorbers and also allow more flexible and elastic diaper constructions, as described for example in U.S. Pat. No. 8834437 B2.

DE 697 19 574 T2 describes a diaper having a backsheet film in the form of a microporous polymer film which contains between 30% and 60% of a polyolefin and between 40% and 80% of calcium carbonate. The film has a "b" value between about zero and about 0.5 and exhibits a thermal shrinkage of less than 2%. The underlayer comprises a layer of a nonwoven material laminated to the film.

EP 3 222 406 B1 describes a process for producing a filled film web from a microporous starting film web. The microporous starting film web is heated to a partially molten state. This has the result that a low melting point polymer component is in the molten state and at least a high melting point polymer component is not in the molten state. Cooling is carried out by passing the partially molten film web through a cooled roller nip.

WO 2015/175593 A1 describes a breathable filled film based on polyethylene. In addition to a high proportion of polyethylene, the film also contains a high proportion of calcium carbonate and a relatively low proportion of a polypropylene. This film is produced by cast extrusion. The described cast film has a relatively low basis weight of only 15 g/m².

While such cast films produced in the cast film process have a low basis weight and a good breathability, they do not fulfill the demands of the now exceptionally high converter speeds in diaper production. They have not kept pace with the increasing converter speeds which result in high impulse stresses especially during deflection and folding of the diaper. This results in mechanical damage, especially breakage of such films parallel to the machine direction. The more severe compression of the diaper, where due to the relatively high converter speed more air must be pressed out of the diaper in a shorter time, can lead to bursting of an insufficiently strong backsheet.

US 2002/0 143 306 A1 describes a breathable film based on polyethylene. This results from combining low-density polyethylene (LLDPE) with ultralow-density polyethylene (ULDPE). The very low melting point of the ULDPE gives rise to problems during laminating with nonwovens since the laminating typically employs hotmelt adhesives having application temperatures of about 150° C. The lower the melting point of the polyethylene, the higher the risk that the adhesive melts holes in the backsheet film. Films according to US 2002/0 143 306 A1 additionally exhibit a high shrinkage in the machine direction. Such films are therefore not suitable for printing with high registration accuracy.

In addition, the ever thinner absorbent cores comprising a high proportion of superabsorber granulates have the result that in the case of conventional backsheet films having a relatively low basis weight, leaks occur and the quality of the diaper thus suffers. The new absorbent core designs too, which comprise for example channels for faster and more uniform liquid distribution, result in high stresses which conventional thin backsheet films having a low basis weight are no longer able to withstand.

All of these abovementioned demands have in recent years prevented the basis weight of breathable backsheet films from being reduced to below a limit of 15 to 16 g/m². Even at these basis weights, conventional backsheet films keep having problems which leads to leaking diapers and has a negative effect on the quality of the diaper. This has the potential for considerable reputational damage to producers of diapers, especially of premium products.

SUMMARY

It is an object of the present invention to provide a breathable film which meets the abovementioned demands. The film shall be robust and printable with high registration accuracy. It shall additionally be suitable for lamination with a nonwoven using a hotmelt adhesive. The film shall enhance the quality of the diapers and meet the demands of diaper production in modern processes.

This object is achieved according to the invention by a breathable film, a process and a use having one or more of the features described herein. Preferred variants are apparent from the claims and the description that follow.

DETAILED DESCRIPTION

The film according to the invention has a specific combination of features not known in backsheet films. This specific combination of features makes it possible also to employ thin films having a low basis weight for production of diapers in modern converter machines at high throughput.

In the case of the film according to the invention, the employed measure for resilience may be the ball drop impact method or the dart drop method or the water column measurement method.

In the ball drop impact method a ball is dropped onto the film and the fall height of the ball is varied.

The dart drop method is performed according to ASTM D1709 and the mass of the dart is varied.

The method of water column measurement is carried out according to EDANA WSP 80.6. The pressure increase is 10 mbar per minute. The test liquid employed is distilled water. The test area is 100 cm² without the supporting sieve. The water column is reported in units of "millimeters".

The following features I to III are combined in the film according to the invention:

I. The film has a specific ball drop impact fall height of more than 100 mm per gram of polymer per square meter, or the specific dart drop of the film is more than 19 g per gram of polymer per square meter, or the specific water column of the film is more than 90 mm per gram of polymer per square meter.

II. The film also has a water vapor permeability of at least 1000 g/m² in 24 hours.

III. In addition to these properties, the film has a breaking elongation in the machine direction of less than 200%.

This inventive combination of features provides a film which is thin, has a low basis weight and meets all of the demands to be used for producing diapers in a highly efficient production process with high converter speeds.

The film according to the invention has much better mechanical properties than conventional backsheet films. These properties are ensured despite an exceptionally low polymer content.

In addition, the film according to the invention has a high water vapor permeability, but nevertheless reliably ensures soakthrough protection.

The invention relates to filled breathable films. These have a high filler content which serves to produce vacuoles in the stretching process which in turn ensure breathability. The filler proportion must be high enough to ensure that stretching not only ensures that microporous pores are formed but also that connections between the pores are present so that the film becomes breathable. Only a microporous film where the pores are interconnected has breathable properties. When producing these breathable films said films are filled to a very high proportion of about 60% with inert material and, after extrusion, subjected to a stretching process. Only this high filler content ensures sufficient breathability. A high filler content also helps with resource conservation and reducing production costs. However, a high filler content has an adverse effect on the strength of the film. The mechanical stability thereof is almost exclusively dependent on the polymer content. When comparing the strength of different films it is advantageous to compare values with the same polymer content per square meter.

In the ball drop impact method used for characterizing the film according to the invention, a steel ball having a diameter of 19 mm and a weight of 25 g is dropped from different heights onto the film stretched over a circular surface. The diameter of the opening onto which the ball falls is 76 mm.

The testing of these achievable fall heights depends substantially on the basis weight of the film. Since mechanical stability is substantially influenced by the polymer content of the film and not by the mineral filler present, the percentage fall height in millimeters divided by the polymer content per square meter is used as a characteristic parameter.

In contrast to conventional backsheet films, the film according to the invention achieves values of more than 100 mm of fall height per gram of polymer per square meter. The specific fall height is by preference more than 120 mm, preferably more than 130 mm, in particular more than 140 mm, in each case per gram of polymer per square meter of film.

It is alternatively possible to use the dart drop method according to ASTM D1709A for characterizing the film according to the invention. This results in values of more than 19 g per gram of polymer per square meter, preferably of more than 20 g per gram of polymer per square meter, in particular more than 21 g per gram of polymer per square meter.

A further method for characterizing the film according to the invention is the specific water column method according to EDANA WSP 80.6. This water column is more than 90 mm per gram of polymer per square meter, preferably more than 100 mm per gram of polymer per square meter, in particular more than 110 mm per gram of polymer per square meter and very preferably more than 120 mm per gram of polymer per square meter.

For characterizing the film, reference is hereinbelow made by way of example to the ball drop method, the two alternative methods dart drop and water column also being expressly included.

The filler content may be determined by known methods of measurement such as ashing: a sample of known starting weight is heated to a temperature at which the polymer is thermally decomposed but the filler is not. A temperature of for example 560° C. has proven advantageous therefor. The sample weight is then remeasured. The polymer content per square meter may be calculated from the difference between the starting weight and the end weight.

A possible alternative to ashing is a TGA measurement where the weight of a sample is continuously measured during heating. This test method can likewise clearly differentiate between polymer and filler and makes it possible to determine the polymer content of the film.

Despite this exceptionally high resilience of the backsheet film according to the invention, said film additionally has a high water vapor permeability. The water vapor permeability defined according to ASTM D6701-01 is more than 1000 g/m$^2$ in 24 hours. The film according to the invention has a water vapor permeability of by preference more than 2000, preferably more than 3000 and in particular more than 3500 g/m$^2$ in 24 hours. Such a high water vapor permeability is unusual in films having such a strong resilience despite such a low basis weight.

In addition, the two abovementioned properties are achieved at a breaking elongation in the machine direction of less than 200%. In a preferred embodiment of the invention, the breaking elongation in the machine direction is in fact less than 170%, preferably less than 150%, in particular less than 130%.

The remaining breaking elongation in the machine direction is used as a parameter for the degree of stretching of the breathable film. The smaller the remaining breaking elongation in the machine direction, the higher the degree of stretching of the breathable film. The breaking elongation is defined in ASTM D882. A test specimen of for example 25.4 mm (1 inch) is cut out and clamped into a suitable test instrument with a clamping length of 50.8 mm. A preliminary force of 0.05 Newtons is applied and followed by a tensile test performed at a speed of 500 mm/min. The quotient of the final breaking of the film by the initial clamping length describes the breaking elongation of the film which is reported in percent. The film according to the invention exhibits an exceptionally low breaking elongation despite a high resilience. This indicates a pronounced stretching of the film in the machine direction. A pronounced stretching of the film in the machine direction results in a high stiffness of the film. In conventional films a pronounced stretching in the machine direction results in such a severe weakening in the cross direction that damage to the conventional backsheet film occurs during folding of the diapers in the converter and/or during donning of the diapers. By contrast, the film according to the invention shows exceptional stability to stresses in the cross direction despite the pronounced stretching in the machine direction, as indicated by the high fall heights in the ball drop impact test.

Due to the weakening of the film in the cross direction, conventional prior art films typically cannot be subjected to such pronounced stretching and these generally have a breaking elongation of more than 250% in the machine direction in order to ensure a minimum of mechanical stability in the cross direction. These conventional relatively weakly stretched films must be passed through the printing machine and the diaper converter at very low web tensions to allow printing with registration accuracy and to avoid excessive constriction in the machine direction, since this would otherwise result in leaks at the lateral edge of the diaper. By contrast, since it has been subjected to very pronounced stretching and has only a small remaining residual elongation in the machine direction, the film according to the invention may be passed through the printing machine and the diaper converter at high speeds. The film is surprisingly also exceptionally stable in the cross direction despite the high stretching in the machine direction. This is most unusual.

Such a combination of features, i.e. a very high resilience per gram of polymer according to the ball drop impact method coupled with very high water vapor permeability and a low breaking elongation in the machine direction, is not known in conventional backsheet films. There are currently no films on the market which unite all of these requirements with one another.

With the film according to the invention it has for the first time been possible to produce an exceptionally thin film having a low basis weight which, at a low polymer usage, is optimally suitable for producing breathable baby diapers, even with modern diaper production processes having very high converter speeds.

This hitherto unknown combination of features is achieved by a specific composition of the film and a targeted selection of polymers in conjunction with a specific production process.

The polymer content of the film according to the invention is relatively low despite these exceptionally stable properties of the film is relatively low despite these exceptionally stable properties of the film. The film has a proportion of polymeric components of less than 55%, preferably less than 50%, in particular less than 45%. However, in order nevertheless to ensure a sufficient stability, the polymer content is more than 25%, preferably more than 30%, in particular more than 35% by weight.

As a preferred filler it is preferable to employ $CaCO_3$ in a particle size of 0.8 to 2 µm. In the stretching process the elastic polymeric proportions of the film are elongated and pores are formed at the edge of the chalk particles with the polymer matrix. The film has a filler content of more than 45%, preferably more than 50%, in particular more than 55%. The solids content is less than 75%, preferably less than 70%, in particular less than 65% by weight.

Many commercial films show insufficient strength. This is often attributable to the employed polymers. The flow characteristics of polyethylenes is described using the melt index MI, typically at a temperature of 190° C. and a loading of 2.16 or 5 kg. A relatively high melt index correlates here with a relatively low average molecular weight of the polymer. It is also true that the higher the melt index of the polymer, the lower the melt viscosity, which is advantageous for a good dispersion of the filler and a high output of the extrusion plant. On the other hand, polymers having a high molecular weight, i.e. a low melt index, are advantageous in terms of mechanical stability, in particular tensile strength and/or toughness.

The film according to the invention has a melt flow index of less than 4 g/10 min, preferably less than 3.5 g/10 min, in particular less than 3.3 g/10 min, in each case at 190° C. and 5 kg. These low melt flow indices imitate a very robust film.

Producing the film according to the invention employs two different linear low-density polyethylene (LLDPE) components. It comprises combining an LLDPE component of low density with an LLDPE component of high density.

The LLDPE component of low density preferably has a density of less than 0.925 g/cm$^3$, in particular less than 0.920 g/cm$^3$. This LLDPE component is preferably employed in a proportion of more than 10%, in particular more than 20%, preferably more than 30%. The proportion of this component is less than 60% by weight, preferably less than 50% by weight, in particular less than 40% by weight.

This first LLDPE component of low density is combined with a second LLDPE component of relatively high density. The density of the second component is preferably more than 0.925 g/cm$^3$, preferably more than 0.930 g/cm$^3$. The proportion of this second LLDPE component of relatively high density is by preference more than 2% by weight, preferably more than 4% by weight, in particular more than 5% by weight. In addition, the proportion of this second LLDPE component of relatively high density is by preference less than 12% by weight, preferably less than 10% by weight, in particular less than 8% by weight.

The first LLDPE component of low density is preferably ethylene-1-hexene copolymer.

It has proven particularly advantageous when at least one LLDPE component has been metallocene catalyzed. It is preferable when the LLDPE component of low density has been produced using a metallocene catalyst.

Polymers as such do not have a sharply defined melting point but rather a melting range, although a crystallite melting point may be attributed to crystalline regions of a polymer. This crystallite melting point is always higher than the melting point or melting range of the noncrystalline constituents. The molten state is described by the property that the shear module tends to zero. In the case of polymers having crystalline regions the latter are then more easily detectable. The shear modulus may be determined according to ISO 6721-1 and 2 for example.

The melting point defined as the peak in a DSC (differential scanning calorimetry) diagram is for the first LLDPE component of low density between 114° C. and 122° C., preferably between 116° C. and 121° C. The melting point of the second LLDPE component is between 120° C. and 128° C., preferably between 121° C. and 126° C.

The LLDPE components employed according to the invention by preference have a melt index according to ISO 1133-1 at 190° C. and 2.16 kg of <2.5 g/10 min, preferably <1.5 g/10 min, in particular <1.2 g/10 min.

The LLDPE component of low density preferably has a melt flow index (MFI) of more than 0.3 g/10 min, preferably more than 0.5 g/10 min, in particular more than 0.8 g/10 min, at 190° C. and 5 kg and/or less than 4 g/10 min, preferably less than 3 g/10 min, in particular less than 2 g/10 min, at 190° C. and 5 kg.

The LLDPE component of relatively high density preferably has a melt flow index (MFI) of more than 0.3 g/10 min, preferably more than 0.5 g/10 min, in particular more than 0.8 g/10 min, at 190° C. and 5 kg and/or less than 5 g/10 min, preferably less than 4 g/10 min, in particular less than 3 g/10 min, at 190° C. and 5 kg.

Only the combination of the two LLDPE components makes it possible to achieve the specific properties of the film according to the invention. The LLDPE component of low density results in the particularly good values in the ball drop impact method, thus achieving a high resilience. However, exclusive use of this component would ensure only insufficient breathability. Only the combination with the LLDPE of relatively high density makes it possible to achieve both good values in impact testing and a sufficiently high water vapor permeability. If only LLDPE of relatively high density were to be employed, the values for water vapor permeability would be satisfactory but the resilience according to the ball drop impact method would be insufficient, thus rendering these films unusable in modern high-throughput diaper manufacturing machines.

In one advantageous embodiment of the invention, the film comprises a polypropylene component. The proportion of this polypropylene component is preferably more than 0.5% by weight, preferably more than 1% by weight and in particular more than 2% by weight. The polypropylene component is preferably present in this case in a proportion of less than 12% by weight, preferably less than 8% by weight, in particular 6% by weight.

The polypropylene component in this case has a melting point, defined as a peak in a DSC diagram, between 158° C. and 165° C., preferably between 160° C. and 164° C. The melt flow index according to ISO 1133-1 at 230° C. and 2.16 kg of the polypropylene component is preferably less than 4.0 g/10 min, in particular less than 3.0 g/10 min.

It has surprisingly been found that the use of this polypropylene component in combination with the two LLDPE components achieves a particularly advantageous film; the polypropylene component has the effect that the film requires less pronounced stretching. This effectively prevents "tiger striping". Tiger striping, which occurs during stretching, is the name given to regions of more and less pronounced stretching which are formed as stripes. In order to prevent this striping the film would actually have to be subjected to more pronounced stretching to better homogenize the film. If this is not carried out the inhomogeneities resulting from nonuniform stretching can result in nonuniform breakage upon use of the film as a backsheet.

It has surprisingly been found that the polypropylene employed in relatively small proportions assists in homogenizing the stretching pattern. It was surprisingly found that the optimized properties of the films according to the invention can be achieved through targeted use of polypropylene within the abovementioned ranges through combination of the two LLDPE components.

The film according to the invention exhibits the exceptionally advantageous properties at a very low basis weight. The basis weight of the film is less than 18 g/m$^2$, in particular less than 16 g/m$^2$. The film is thus also exceptionally thin. The thickness of the finished film is preferably less than 16 µm, preferably less than 14 µm, in particular less than 12 µm.

In order nevertheless to ensure a sufficient thickness such that the film cannot be penetrated by the large particle size superabsorber granulates, the thickness of the film is preferably more than 4 µm, preferably more than 6 µm, in particular more than 8 µm.

The film according to the invention is achieved by combining a very specific composition with a very specific mode of production. The inventive properties of the film are realized through targeted use of blow extrusion. The blow extrusion upstream of the stretching makes it possible to achieve the film properties according to the invention on the basis of the specific composition.

It has surprisingly been found that the upstream blow extrusion allows the film to be subjected to much more pronounced stretching in the machine direction in the subsequent stretching process. The upstream blow extrusion process imparts the film according to the invention with sufficient strength also in the cross direction and the strength in the cross direction is therefore retained even in the case of pronounced stretching of the film in the machine direction. This affords a film which has a very high stiffness in the machine direction, thus allowing it to be run at a very high converter speed in diaper production, but simultaneously also exhibits a strength in the cross direction sufficient to prevent tearing or damage to the film such as occurs upon pulling the diaper ears at the backsheet during subsequent use.

The film web is subjected to the stretching process to produce the microporosity. According to the invention at least one stretching in the machine direction (MD) is carried out. An additional stretching in the cross direction (CD) may also be carried out. Ring rolling would also be possible in principle. Stretching of the film is to be understood as an expansion of the film in a specified direction. This results in a reduction in film thickness. The film may have been stretched in the machine direction (MD) for example using a stretching line which comprises one or more rollers. The rollers preferably run at different speeds.

According to the invention the film is preferably stretched by more than 200%, especially preferably more than 280%, by preference more than 300%, in particular more than 320%. The stretching of the film after the blow extrusion in the machine direction is less than 400%, preferably less than 365% and in particular less than 350%. The stretching by preference employs a temperature of more than 70° C., preferably more than 80° C., in particular more than 90° C. The temperature during stretching in the machine direction is by preference less than 120° C., preferably less than 110° C., in particular less than 100° C.

The stretching of the film in the machine direction causes stresses in the film, as a result of which reheating causes the film to recover, for example when the film is reheated in the printing process to dry the ink or else is reheated with the nonwoven in the laminating process during diaper production. In order to realize the required registration accuracy of the printed backsheet film, this propensity for shrinkback must be minimized.

The recovery properties were measured using MD hot shrinkage as a measured parameter: a square film specimen of 10 cm×10 cm in size was cut out of the film, immersed in an 80° C. water bath for 30 seconds and subsequently quenched in cold water. The film is then remeasured to determine the change in length in the machine direction and the cross direction. A shortening of the film by 2 mm for example then corresponds to a hot shrinkage of 2%.

In a particularly advantageous variant of the invention, the film has a shrinkage in the machine direction of less than 4%, preferably less than 3.5%, in particular less than 3%. Such a low shrinkage allows sufficient registration consistency for problem-free processing of the film.

To control the MD heat shrinkage, the film is passed over further temperature-controlled rollers immediately after the stretching process. It has proven particularly advantageous for this heat treatment process when in this process step the film is heated over 2 to 4 rollers to a temperature between the stretching temperature and the melting point of the polymers. An excessively low temperature results in only insufficient reduction of MD heat shrinkage while an excessively high temperature would cause the pores formed in the stretching process to melt shut again, thus considerably reducing breathability. In addition to the temperature elevation, the heat treatment process may be assisted by introducing a slight speed reduction via the temperature-controlled rollers to allow the just-stretched film to slightly recover.

According to the invention, 5% to 20% recovery in the abovementioned temperature window has proven advantageous for optimizing shrinkage. To complete the heat treatment process, the film is passed over one or more cooled rollers in order to fix the stretched and heat-treated film in the resulting state. These cooling rollers are preferably operated in the temperature range between about 30° C. and 60° C.

A decisive factor for the characteristic properties of the film according to the invention is the upstream blow extrusion. This preferably employs a blow-up ratio of more than 1:1.5, preferably more than 1:2.0, in particular more than 1:2.5. The blow-up ratio in the blow extrusion is preferably less than 1:4.5, preferably less than 1:4.0, in particular less than 1:3.5.

According to the invention, the film is employed as a backsheet in a diaper.

In addition to the breathable film itself the invention also comprises variants in which the film is combined, for example, with other materials, for example a nonwoven. The film according to the invention may be employed either as a single backsheet or as a nonwoven-film laminate. The film may be joined to a nonwoven for example using adhesive. The nonwoven-film laminate may also be produced by a thermobonding process. To this end the film and/or the nonwoven may be heated using two heated rollers either all over or in a punctiform fashion. For example, an embossing roller may be employed with a smooth roller, for example a steel roller, as a backing roller. The film and/or the nonwoven may be incipiently melted via high temperature and pressure. This allows the film and the nonwoven to be joined to one another. Nonwoven-film laminates may also be produced by thermolamination. In addition or as an alternative, nonwoven-film laminates may also be produced using ultrasonic lamination, for example using Hermann Ultraschall technology.

The produced nonwoven-film laminates may be subjected to further processing in known fashion which may also include a stretching in the machine direction and/or a stretching in the cross direction or a stretching in both directions. Further processing of single backsheets is also possible.

The invention further comprises absorbent articles where the film according to the invention is employed. The absorbent article is preferably in the form of a diaper, in particular in the form of a baby diaper.

These absorbent articles generally comprise an absorbent core, an upper layer and a lower layer. The film according to the invention is preferably used in the lower layer.

In the absorbent article according to the invention the film according to the invention may be joined to a nonwoven. The film or the film-nonwoven laminate may also be provided with elastic ears, so-called front and/or back ears. These may either be adhesively bonded to the film or else thermobonded. The absorbent core of the absorbent article preferably comprises a superabsorber encapsulated with a fabric. An ADL (acquisition-distribution layer) may also be employed. This is described for example in US 2005/0267429 A1.

The absorbent core may be provided with channels. The absorbent article comprises not only the backsheet but also a topsheet. The topsheet may be provided with a nonwoven. The topsheet may at least in part be joined to the backsheet. The topsheet may be laminated to the backsheet with a hotmelt adhesive for example.

The invention is hereinbelow explained with reference to an example 1, without any intention to limit the invention thereto.

The following components are employed in this example 1:
- 55% calcium carbonate as a mineral filler, Imerys Filmlink 400
- 36% LLDPE Exceed™ XP 8318 from ExxonMobil
- 6% LLDPE Dowlex™ SC2108 G from DowDuPont
- 3% PP Borpact™ BC918CF from Borealis.

The employed filler is an inorganic filler in the form of calcium carbonate, preferably having a particle size of 0.8 to 2 μm.

The LLDPE Exxon Exceed XP 8318 is the first LLDPE component of relatively low density. This LLDPE is preferably metallocene-catalyzed. It has proven particularly advantageous when an ethylene-1-hexene copolymer is employed in this case. This LLDPE has a density of 0.918 g/cm$^3$ according to ASTM D1505, a melt flow index of 1.0 g/10 min (at 190° C./2.16 kg) according to ASTM D1238 and a peak melt temperature of 121° C. according to the ExxonMobil method.

The LLDPE Dowlex™ SC2108 G is the second LLDPE component of relatively high density. The density is 0.935 g/cm$^3$. The melt flow rate is 2.6 g/10 min (at 190° C., 2.16 kg) according to ISO 1133.

The Borpact™ BC918CF is a highly crystalline polypropylene having a density of 0.905 g/cm$^3$. The melt flow rate (at 230° C./2.16 kg) according to ISO 1133 is 3.0/10 min. The melt temperature (DSC) according to ISO 3146 is 166° C.

To produce the inventive film, the polymer constituents together with the mineral fillers are heated to a temperature markedly above the melting temperature of the polymer constituents (for example above 200° C.) and melted together in an extruder, for example a compounding extruder.

According to the invention this is followed by a blow extrusion. The blow extrusion process forms a blown bubble. The film bubble formed may be collapsed and sliced at the ends to form two film webs, each of which may be used as a starting film web.

The blown film process uses a blow-up ratio of 1:2.9.

The primary basis weight of the film is 46.2 g/m$^2$

In the subsequent monoaxial stretching process, the film is stretched by altogether 330% in the machine direction. This overall stretching factor results from the actual stretching in the machine direction of 350% at a roller temperature of 95° C. and subsequent heat treating at a temperature of 106° C., wherein a shrinkback of 6% is allowed on the heat treatment rollers.

This results in a basis weight of the film of 14 g/m$^2$.

The polymer content of the film is 6.3 g/m$^2$.

The inventive film has the following properties:
- absolute ball drop impact fall height: 900 mm
- specific ball drop impact fall height: 142.8 mm per gram of polymer
- water vapor permeability: 4000 g/m$^2$ in 24 hours
- MD breaking elongation: 120%
- MD heat shrinkage: 3%

The inventive film exhibits particularly advantageous product properties for use in a baby diapers and also meets the demands of processing in modern diaper production plants with their high throughputs.

In the following table the inventive film described above in example 1 is compared with conventional, commercial breathable backsheet films according to examples 2 to 5.

For explanation of the table, reference is hereinbelow made by way of example only to the ball drop fall height.

The poorest values are shown by the film according to example 3 with a specific ball drop fall height of only 84.9 mm. Example 3 relates to a film where no stretching of the film in machine direction (MDO stretching) was carried out, but rather the film was produced by MD/CD ring rolling. In addition, this film further comprises only one LLDPE component. However the film comprises a PP component.

The film according to example 5 also comprises only one LLDPE component and a PP component. However, this film was produced using a stretching in the machine direction (MDO stretching) and compared to the preceding example a ball drop fall height of 87.7 mm is therefore achieved.

The film according to example 4 was also produced using a stretching in the machine direction (MDO stretching). Although the film comprises no PP component it has a higher ball drop fall height compared to example 5 of 89.7 mm since it was produced with two LLDPE components.

Of the conventional commercial films, example 2 shows the best values with a ball drop fall height of 95.4 mm, wherein this film was produced using a stretching in the machine direction (MDO stretching) and comprises two LLDPE components and a PP component.

Compared to all of these conventional commercial films, the inventive film according to example 1 has far and away the best values with an exceptional ball drop fall height of 142.9 mm. This best value is achieved despite an exceptionally low basis weight of only 14 g/m$^2$.

TABLE

Comparison of inventive film with conventional films

| | Characterization | Polymer content [g/m$^2$] | Measurement of ball drop impact | | Measurement of water column WSP 80.6 Measurement 1 [mm] |
|---|---|---|---|---|---|
| | | | Average value [mm] | Spec. ball drop [mm per g of polymer] | |
| Example 1 | Inventive film | 6.3 | 900 | 142.9 | 729 |
| Example 2 | 16 gsm blown film with inline MDO stretching 2 LLDPE + PP | 7.23 | 690 | 95.4 | 813 |

TABLE-continued

Comparison of inventive film with conventional films

| | | | | | |
|---|---|---|---|---|---|
| Example 3 | 15 gsm blown film with MD/CD ring rolling only one LLDPE + PP | 5.89 | 500 | 84.9 | 302 |
| Example 4 | 15 gsm blown film with in-line MDO stretching 2 LLDPE but no PP | 7.84 | 700 | 89.3 | 623 |
| Example 5 | 15 gsm blown film with in-line MDO stretching only one LLDPE + PP | 5.7 | 500 | 87.7 | 494 |

| | Measurement of water column WSP 80.6 | | | Dart drop ASTM D1709A | | MFI |
|---|---|---|---|---|---|---|
| | Measurement 2 [mm] | Average value [mm] | Spec. water column [mm per g of polymer] | Average value [g] | Spec. dart drop [g per g of polymer] | g/10 min 190° C., 5 kg |
| Example 1 | 790 | 759.5 | 120.6 | 138 | 21.9 | 3.2 |
| Example 2 | 617 | 615 | 85.1 | 115 | 15.9 | 4.5 |
| Example 3 | 317 | 309.5 | 52.5 | 82 | 13.9 | 7.1 |
| Example 4 | 642 | 632.5 | 80.7 | 90 | 11.5 | 4.4 |
| Example 5 | 433 | 463.5 | 81.3 | 99 | 17.4 | 4.1 |

The invention claimed is:

1. A breathable film, comprising:
   a polymer film having a specific ball drop fall height that is more than 100 mm per gram of polymer per square meter or a specific dart drop that is more than 19 g per gram of polymer per square meter or a specific water column that is more than 90 mm per gram of polymer per square meter;
   a water vapor permeability of at least 1000 g/m² in 24 hours;
   and a breaking elongation in a machine direction that is less than 200%.

2. The film as claimed in claim 1, wherein the film has a basis weight of less than 17 g/m².

3. The film as claimed in claim 1, wherein the film has a melt flow index of less than 4 g/10 min at 190° C. and 5 kg.

4. The film as claimed in claim 1, wherein the film has a shrinkage in the machine direction of less than 4%.

5. The film as claimed in claim 1, wherein the film has a filler content of more than 20% by weight and less than 90% by weight.

6. The film as claimed in claim 1, wherein the film comprises an LLDPE component of relatively low density, wherein the density of this relatively low density LLDPE component is less than 0.925 g/cm³;
   and the film has an LLDPE component of relatively high density, wherein the density of this relatively high density LLDPE component is more than 0.925 g/cm³.

7. The film as claimed in claim 6, wherein a proportion of the LLDPE component of relatively low density is more than 10% by weight and is less than 60% by weight.

8. The film as claimed in claim 7, wherein the proportion of the LLDPE component of relatively high density is more than 2% by weight and is less than 12% by weight.

9. The film as claimed in claim 6, wherein the film comprises a polypropylene component in a proportion of more than 0.5% by weight and less than 12% by weight.

10. The film as claimed in claim 9, wherein the film has a thickness of less than 16 μm and more than 4 μm.

11. A process for producing the breathable film according to claim 1, comprising the steps of:
    producing a composition comprising
    fillers,
    an LLDPE component of low density, and
    an LLDPE component of high density,
    blow extruding the composition to form a film,
    stretching the film in a machine direction,
    passing the film over at least one temperature-controlled roller to reduce a propensity for shrinkback.

12. The process as claimed in claim 11, wherein the film is stretched by more than 280% and less than 400%.

13. The process as claimed in claim 11, wherein the film is stretched at a temperature of more than 70° C. and less than 120° C.

14. The process as claimed in claim 11, wherein a blow-up ratio for the blow extruding is more than 1:1.5 and less than 1:4.5.

15. A diaper comprising a backsheet formed of the breathable film as claimed in claim 1.

* * * * *